United States Patent [19]
Craig

[11] Patent Number: 6,158,712
[45] Date of Patent: Dec. 12, 2000

[54] MULTILAYER INTEGRATED ASSEMBLY HAVING AN INTEGRAL MICROMINIATURE VALVE

[75] Inventor: Stephen R. Craig, Wilmington, Del.

[73] Assignee: Agilent Technologies, Inc., Santa Clara, Calif.

[21] Appl. No.: 09/174,134

[22] Filed: Oct. 16, 1998

[51] Int. Cl.[7] .................................................. F16K 31/145
[52] U.S. Cl. ........................ 251/61.1; 251/61.2; 251/331
[58] Field of Search ................................. 251/61.1, 61.2, 251/331

[56] References Cited

U.S. PATENT DOCUMENTS

| | | | |
|---|---|---|---|
| 3,154,286 | 10/1964 | MacFarland, Jr. | 251/331 |
| 3,530,568 | 9/1970 | Owczarski et al. | |
| 3,538,744 | 11/1970 | Karasek . | |

(List continued on next page.)

OTHER PUBLICATIONS

Manz et al.; "Design Of An Open–Tubular Column Liquid Chromatograph Using Silicon Chip Technology" (1990) Sensors & Actuators B1, pp. 249–255.

Fan et al., "Micromachining Of Capillary Electrophoresis Injectors And Separators On Glass Chips And Evaluation Of Flow At Capillary Intersections" (1994);Anal. Chem. 66(1):177–184.

Jorgenson et al., "Liquid Chromatography In Open–Tubular Columns" (1983) J. Chromatogr. 255:335–348.

Manz et al., "Planar Chips Technology for Miniaturization And Integration Of Separation Techniques Into Monitoring Systems—Capillary Electrophoresis On A Chip" (1992) J. Chromatogr. 593:253–258.

Harrison et al., "Towards Miniaturized Electrophoresis And Chemical Analysis Systems On Silicon: An Alternative To Chemical Sensors" (1993) Sensors & Actuators B 10, pp. 17–116.

Manz et al., "Micromachining Of Monocrystalline Silicon And Glass For Chemical Analysis Systems: A Look Into Next Century's Technology Or Just A Fashionable Craze?" (1991); Trends Anal. Chem. 10 (5):144–149.

Manz et al., "Planar Chips Technology For Miniaturization Of Separation Systems: A Developing Perpective In Chemical Monitoring" (1993) Adv. Chrom. 31:1–66.

*Primary Examiner*—Kevin Shaver
*Assistant Examiner*—John Bastianelli

[57] ABSTRACT

A microminiature valve includes a housing having a cavity, and a diaphragm having an array of a plurality of redundant, generally concentric, annular seals on an underside of the diaphragm, wherein the diaphragm is positioned within the cavity so as to define upper and lower cavity sections and wherein the array is located opposite a valve seat formed on a lower cavity surface, and wherein the valve seat incorporates a central port and a peripheral port, such that a signal fluid stream provided between the central port and the peripheral port may be controlled by displacing the annular seals to and from the valve seat, thereby respectively interrupting or permitting the flow of the signal fluid stream. The upper cavity section includes a control port for supplying a pressurized control fluid to the upper cavity and accordingly to the upper side diaphragm, so as to effect a pressure differential for movement of diaphragm with respect to the valve seat. The array includes a plurality of redundant, concentric annular seals, wherein at least one of the annular seals is sufficiently positionable for independently effecting a fluid-tight barrier to fluid flow when impressed upon the valve seat, even in the presence of a particle lodged between the valve seat and the array, such that the contemplated microminiature valve is therefore unlikely to fail when one or more fluid-borne particles becomes lodged between the valve seat and the array. The microminiature valve may be provided in a multilayer integrated assembly constructed using a planar foldable substrate and an intermediary substrate.

4 Claims, 5 Drawing Sheets

U.S. PATENT DOCUMENTS

| | | |
|---|---|---|
| 3,678,570 | 7/1972 | Pauloris et al. . |
| 4,220,276 | 9/1980 | Weisert et al. . |
| 4,245,769 | 1/1981 | Meginnis . |
| 4,474,889 | 10/1984 | Terry et al. . |
| 4,794,940 | 1/1989 | Albert et al. ......... 251/61.2 X |
| 4,809,589 | 3/1989 | Bertrand ............... 92/98 |
| 4,858,883 | 8/1989 | Webster ............... 251/61.1 |
| 4,869,282 | 9/1989 | Sittler et al. ......... 251/61.1 X |
| 4,891,120 | 1/1990 | Sethi et al. . |
| 4,905,497 | 3/1990 | Shindo et al. . |
| 4,908,112 | 3/1990 | Pace . |
| 4,935,040 | 6/1990 | Goedert . |
| 4,943,032 | 7/1990 | Zdeblick ............... 251/11 |
| 5,064,165 | 11/1991 | Jerman ............... 251/61.1 |
| 5,132,012 | 7/1992 | Miura et al. . |
| 5,193,781 | 3/1993 | Willbanks ......... 251/129.16 X |
| 5,194,133 | 3/1993 | Clark et al. . |
| 5,236,118 | 8/1993 | Bower et al. . |
| 5,323,999 | 6/1994 | Bonne et al. ......... 251/331 X |
| 5,325,880 | 7/1994 | Johnson et al. ......... 251/129.01 X |
| 5,335,584 | 8/1994 | Baird ............... 92/98 |
| 5,452,878 | 9/1995 | Gravesen et al. ......... 251/129.02 |
| 5,453,769 | 9/1995 | Schantz et al. . |
| 5,500,071 | 3/1996 | Kaltenbach et al. . |
| 5,567,868 | 10/1996 | Craig et al. . |
| 5,571,410 | 11/1996 | Swedberg et al. . |
| 5,641,400 | 6/1997 | Kaltenbach et al. . |
| 5,658,413 | 8/1997 | Kaltenbach et al. . |
| 5,792,943 | 8/1998 | Craig . |
| 5,836,571 | 11/1998 | Streitman et al. ......... 251/331 |
| 5,863,024 | 1/1999 | Blind et al. ......... 251/129.06 X |
| 5,932,799 | 8/1999 | Moles ............... 251/61.1 X |

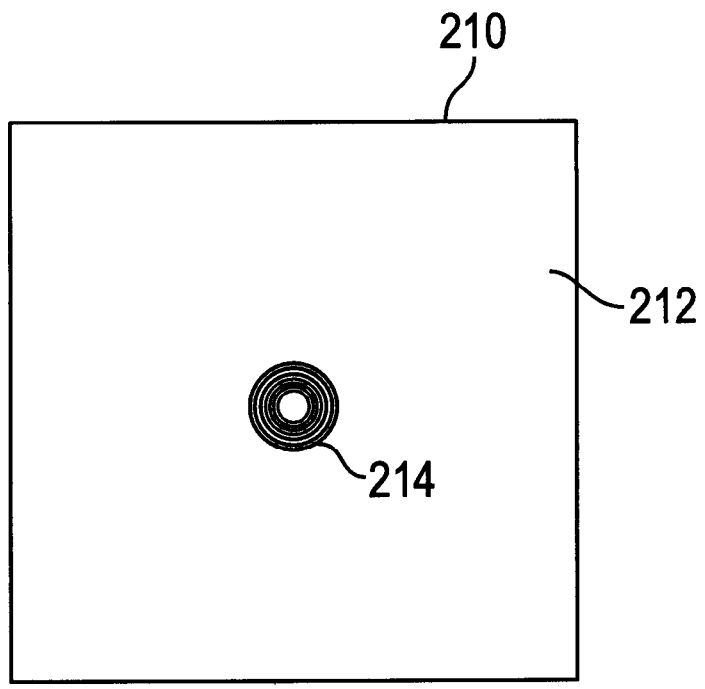

MULTILAYER INTEGRATED ASSEMBLY HAVING AN INTEGRAL MICROMINIATURE VALVE

CROSS REFERENCE TO RELATED APPLICATION

The present invention is related to co-pending, commonly assigned U.S. patent application Ser. No. 08/846,607, filed on Apr. 30, 1997 in the name of Stephen R. Craig, the contents of which are incorporated herein by reference.

FIELD OF THE INVENTION

The present invention relates generally to miniaturized planar device technology for liquid and gas phase analysis. More particularly, the invention relates to a multilayer integrated assembly for effecting fluid handling functions, wherein there is provided one or more integral, microminiature valves.

BACKGROUND OF THE INVENTION

In sample analysis instrumentation, and especially in separation systems such as gas or liquid chromatography and capillary electrophoresis systems, smaller dimensions will generally result in improved performance characteristics and at the same time result in reduced production and analysis costs. In this regard, miniaturized planar devices provide more effective system design and result in lower overhead due to decreased instrumentation sizing. Additionally, miniaturized planar devices enable increased speed of analysis, decreased sample and solvent consumption and the possibility of increased detection efficiency.

Several approaches towards miniaturization have developed in the art. The conventional approach provides etched planar devices on glass, silicon, metal, or ceramic substrates of moderately small size. For example, planar devices may be etched in a wafer that receives a superimposed cover plate. In some approaches, certain fluid handling functions have not been successfully integrated into the planar device and accordingly must be effected by the attachment of conventional devices, such as fused silica capillary tubing, to the planar device.

More recent approaches have used micromachining of silicon substrates and laser ablation of organic nonmetallic substrates to provide structures of much smaller size (i.e., microstructures) on the substrate. For example, there has been a trend towards providing planar systems having capillary separation microstructures. See, for example: Karasek, U.S. Pat. No. 3,538,744; Terry et al., U.S. Pat. No. 4,474,889; Goedert, U.S. Pat. No. 4,935,040; Sethi et al., U.S. Pat. No. 4,891,120; Shindo et al, U.S. Pat. No. 4,905,497; Miura et al., U.S. Pat. No. 5,132,012. Silicon provides a useful substrate in this regard since it exhibits high strength and hardness characteristics and can be micromachined to provide structures having dimensions in the order of a few micrometers.

A drawback in the silicon micromachining approach to miniaturization is the chemical activity and chemical instability of certain materials used for substrates, such as silicon, quartz or glass, which are commonly used in systems for both capillary electrophoresis (CE) and chromatographic analysis systems. Accordingly, Kaltenbach et al., in commonly-assigned U.S. Pat. No. 5,500,071, and Swedberg et al., in commonly-assigned U.S. Pat. No. 5,571,410 disclose a miniaturized total analysis system comprising a miniaturized planar column device for use in a liquid phase analysis system. The miniaturized column device is provided in a substantially planar substrate, wherein the substrate is comprised of a material selected to avoid the inherent chemical activity and pH instability encountered with silicon and prior silicon dioxide-based device substrates. More specifically, a miniaturized planar column device is provided by ablating component microstructures in a polymer substrate using laser radiation. The miniaturized column device is described as being formed by providing two substantially planar halves having microstructures thereon, which, when the two halves are folded upon each other, define a sample processing compartment featuring enhanced symmetry and axial alignment.

However, although the foregoing techniques are useful in the fabrication of miniaturized planar devices for effecting fluid handling functions in sample analysis systems, there are significant disadvantages to the prior art approaches. One significant problem remains in providing exact alignment of complementary pairs of microstructures that are respectively provided in a planar substrate and its cover plate, or in a pair of planar substrates, when such microstructures are intended to be superimposed so as to form one or more channels capable of performing a fluid handling function in a unitary assembly. For some applications, prior art planar technology has not produced a sufficient degree of alignment between the superimposed microstructures.

Another problem arises in the attempt to effect hermetic sealing of the superimposed surfaces. This step is generally carried out using adhesives which may not fully isolate the channels thus resulting in cross-channel leakage. Conventional approaches can be prone to failure, leakage, or to degradation induced by adverse conditions, such as high temperature environments, or by the destructive nature of certain gases or liquids that may be present in the channels.

Still another problem arises because silicon substrates, and most ablatable materials such as polyimides, do not offer a sufficient combination of thermal and mechanical characteristics such that the substrate is usable in certain applications. For instance, silicon materials are not ductile and cannot be folded, shaped, etc.; ablatable materials exhibit a low coefficient of thermal conductivity and are not susceptible to rapid and uniform heating or cooling, nor do they offer sufficient strength or ductility such that an ablatable substrate may be configured as a connecting member, housing, or support for other components in a sample analysis system. Ablatable materials are expressly selected for their propensity to ablate upon the application of heat, and thus are not considered to be as robust and impervious to adverse (e.g., high-temperature) environments in comparison to metals and metal alloys.

Another problem arises in a prior art microminiature valve that is constructed of "hard" (i.e., non-resilient) materials, such as silicon, in the valve seat and/or the movable member that contacts the valve seat. Such valves can fail when one or more fluid-borne particles of sufficient size becomes lodged between the valve seat and the movable member, and effectively precludes the valve from closing. To accommodate such an occurrence, some designs incorporate "soft" (i.e., resilient) materials; however, resilient materials cannot withstand the high-temperature environment and harsh chemicals typically encountered by a valve situated in a modern chromatographic instrument.

Accordingly, there is a need for a novel microminiature valve, and an integrated assembly incorporating such a valve, having improved pneumatic characteristics and thermal characteristics, and which is less susceptible to failure due to a high-temperature environment, the presence of harsh chemicals, or to particles which may block proper operation of the valve.

SUMMARY OF THE INVENTION

The present invention is directed to a novel microminiature valve constructed to include a cavity, a diaphragm having an array of a plurality of redundant, generally concentric, annular seals on an underside of the diaphragm, wherein the diaphragm is positioned within the cavity so as to define upper and lower cavity sections and wherein the array is located opposite a valve seat formed on a lower cavity surface, and wherein the valve seat incorporates a central port and a peripheral port, such that a signal fluid stream provided between the central port and the peripheral port may be controlled by displacing the annular seals to and from the valve seat, thereby respectively interrupting or permitting the flow of the signal fluid stream. The upper cavity section includes a control port for supplying a pressurized control fluid to the upper cavity and accordingly to the upper side diaphragm, so as to effect a pressure differential for movement of diaphragm with respect to the valve seat. The array includes a plurality of redundant, concentric annular seals, wherein at least one of the annular seals is sufficiently positionable for independently effecting a pressure tight barrier to fluid flow when impressed upon the valve seat, even in the presence of a particle lodged between the valve seat and the array, such that the contemplated microminiature valve is therefore unlikely to fail when one or more fluid-borne particles becomes lodged between the valve seat and the array.

For the purposes of this description, an "annular seal" refers to a ring-like raised surface in the diaphragm having a sufficiently closed geometry such that the seal may be impressed upon the valve seat to contain or block fluid flow between a first region within and circumscribed by the seal, and a second region outside of the seal. "Annular" refers not only to circular geometries, but also to oval, oblong, triangular, square, rectilinear, polyhedral, and other closed configurations. The size and geometry of one or more obstructing particles will, of course, determine the effectiveness of the array; for example, a particle of sufficiently large size that obstruct sub some portion of each and every one of the annular seals is therefore likely to prevent at least one of the annular seals from closing fully upon the valve seat. Accordingly, the present invention contemplates the use of an array of redundant annular seals, wherein the array designed to include a sufficient number of substantially independently-operable seals, the seals having sufficient geometries and dimensions, wherein the array is operable to achieve a fluid tight seal even in the presence of one or more particles that may become lodged between the array and the valve seat during the operation of the particular embodiment of the contemplated microminiature valve. Such dimensions, geometries, and the like are necessarily determined according to the particular application of the microminiature valve, and the embodiments described herein are meant to be exemplary but not limiting.

In another aspect of the invention, the contemplated microminiature valve also maintains its effectiveness without resort to the use of "soft" (i.e., resilient) materials for construction of the diaphragm or valve seat. In one aspect of the invention, preferred embodiments of the microminiature valve include a diaphragm provided in the form of a thin, flexible, planar layer having the array of annular seals formed therein by etching, electroforming, or similar processes. Preferred materials for the diaphragm include metals and metal alloys.

The present invention is also directed to a multilayer integrated assembly (hereinafter, "integrated assembly") for effecting fluid handling functions, wherein the aforementioned novel microminiature valve is included in the integrated assembly and the diaphragm, valve seat, and central, peripheral, and control ports are integrated as surface features on planar substrates that are joined together to form the integrated assembly.

In a preferred embodiment of the integrated assembly, the diaphragm is incorporated as a surface feature on or within a specialized intermediary substrate which is then interposed between first and second planar substrates which in turn are joined to form the integrated assembly.

A particularly preferred embodiment of the integrated assembly includes: (a) a planar device having a cavity therein defined by closure of first and second component sections at a linear fold means; (b) a diaphragm located in the cavity so as to generally divide the cavity into an upper cavity portion and a lower cavity portion, which respectively include an upper cavity surface and a lower cavity surface; (c) a valve seat located in the lower surface, having central and peripheral ports on the valve seat for respectively effecting input and output flows of a signal fluid stream with respect to the lower cavity; (d) a control port located on the upper cavity surface for providing a pressurized control fluid to the upper cavity; (e) an array of plural, redundant, annular seals formed on the underside of the diaphragm, and thus located opposite the valve seat, wherein the array is selectably movable to and from the valve seat in response to a corresponding pressure applied by the control fluid, thus controlling the position of the diaphragm and wherein at least one of the annular seals accordingly positionable with respect to the valve seat for modulating the flow of the signal fluid stream.

In another aspect of the invention, preferred embodiments of the integrated assembly also include surface features in the form of complementary microstructures formed on one or more planar substrates by etching, electroforming, or similar processes. The complementary microstructures are superimposed in a controlled manner by operation of a linear fold means also formed in the substrate by an etching or similar process. Such microstructures are contemplated as including channels (that may be superimposed to form fluid conduits), apertures, conduit apertures, sample processing compartments, and the like.

In another aspect of the invention, the integrated assembly includes a planar substrate having at least first and second component sections separated by a linear fold means, wherein the substrate is comprised of a material that is ductile in the region of the linear fold means and substantially inextensible in the regions defined by the component sections, such that the two adjacent component sections may be superimposed by folding the component sections upon each other about the fold axis. Upon superimposition of the component sections, the complementary microstructures are precisely co-located and superimposed. The linear fold means constrains the co-location of the microstructures with extreme accuracy due to the inextensibility of the substrate with respect to the fold axis. The preferred substrate material for one or more of the planar substrates is a metal or metal alloy, such as nickel or stainless-steel, that exhibits appropriate thermal and mechanical characteristics such that the component sections of the substrate may be superimposed by folding the substrate at the linear fold means, then bonded and optionally shaped, to provide a unitary assembly having a useful configuration.

The ability to exert rigid computerized control over the etching and/or electroformation of the desired microstructures enables extremely precise microstructure formation, which, in turn, enables the formation of such surface features as a concentric array of annular seals, with associated ports and complementary micro-channels etched in two substantially planar component sections, whereby those component sections may be aligned by use of the linear fold means acting in concert with the fold relief, to define a composite microminiature valve compartment. Formation of the subject surface features while the planar substrates are in the open configuration enables a wide variety of surface treatments and modifications to be applied to the interior surfaces of the channels before formation of the compartment.

In another aspect of the invention, the diaphragm is provided by electroforming and the associated port microstructures in the planar substrate are provided by etching.

In another aspect of the invention, a specialized intermediary substrate is constructed to include the aforementioned diaphragm and ports so as to form the novel microminiature valve when interposed between the mating surfaces of first and second component sections.

In another aspect of the invention, the integrated assembly optionally includes n component sections and (n−1) linear fold means, wherein n equals three or more, wherein the component sections are closed upon one another in a Z-fold configuration.

In the preferred embodiments described herein, bonding of the superimposed component sections is preferably accomplished by use of a diffusion bonding technique.

Accordingly, the contemplated embodiments of an integrated assembly provides fluid-handling structures in substrate materials resistant to high temperatures and adverse environments, and is desirable for supporting fluid flow through, for example, a fluid circuit in a sample processing or sample analysis system. The integrated assembly will be seen to facilitate reliable connections between external fluid-handling functional devices (such as fittings, sensors, and the like) by use of a single planar device for the provision of a plurality of flow paths. The fluid-handling functional devices that connect to the integrated assembly are preferably constructed to be surface-mounted, which has been found to offer reliable, fluid-tight connection without the complexity and difficulty of conventional connections. The number and complexity of external connections, which would otherwise undesirably increase the volume of the flow system, are also decreased. Another advantage is that the reliability of the fluid-bearing connections is improved.

A further advantage of the present invention is that one or more microminiature valves and multiple fluid-handling functional devices may be coordinated and assembled in a smaller volume than is possible in prior art systems. This results from inclusion of the valve functions, pneumatic channels, and other fluid handling functions into the integrated assembly, and thus many of the fluid flow paths are kept within the integrated assembly, which is itself quite compact and amenable to construction in a variety of shapes and configurations. A large number of novel microminiature valves may be integrated into the integrated assembly in a fashion that heretofore would be difficult if not impossible to accomplish using conventional valves and fittings.

The microminiature valves provided by the invention also reduce the cost and complexity of a flow system, which is desirable during the stages of manufacturing, assembly, repair, or modification of the analytical instrument in which the integrated assembly may be situated. Also, considerable cost savings and improved reliability are realized by reduction of the number of connections necessary to achieve multiple flow paths.

The use of conventional electroforming and etching processes to form the desired microstructures in the preferred metal or metal alloy substrates increases the ease of fabrication and lowers the per-unit manufacturing costs in the subject devices as compared to prior approaches, such as approaches that involve micromachining in silicon.

The integrated assembly is robust (e.g., exhibits an ability to withstand adverse environments, mishandling, and operation at elevated temperature), is easily cooled or heated, and is sufficiently strong and rigid so as to serve as a connecting member, support member, chassis, housing, or the like. In this regard, integrated assemblies formed according to the invention have the unusual feature of being robust yet quite inexpensive, and thus may be designed as disposable miniaturized assemblies.

Preferred embodiments of the present invention will find advantageous use in a gas or liquid phase sample analysis system.

Accordingly, the subject invention finds potential application not only in many applications now served by conventional valves, but also in complex or miniature fluid flow control systems, in microfluidic systems, and in systems for monitoring, control, and/or analysis of fluid streams found in chemical, biological, biochemical, pharmaceutical, and medical processes and the like.

BRIEF DESCRIPTION OF THE FIGURES

FIG. 3 is a simplified plan view of the diaphragm of FIGS. 2 and 2A.

DETAILED DESCRIPTION OF THE INVENTION

Figure 1:
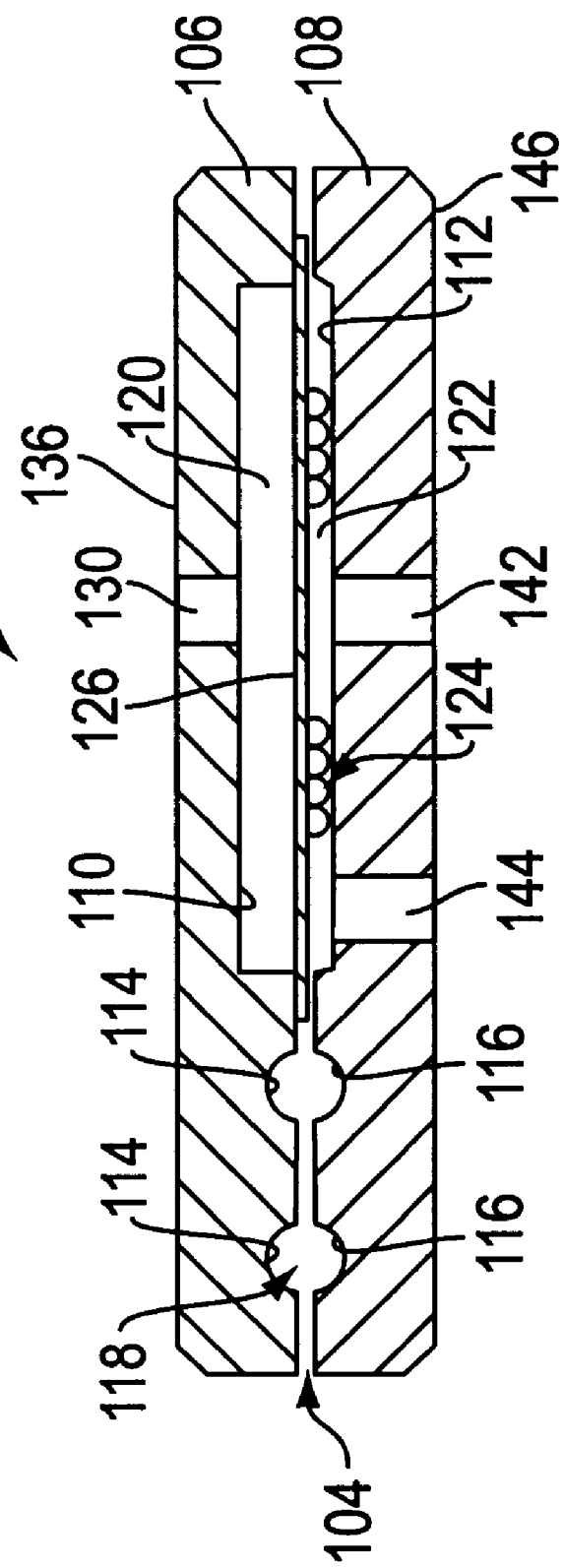
FIG. 1 is a cross-sectional axial view of a housing that incorporates a novel microminiature valve, preferably formed by the alignment of a diaphragm and complementary microstructures in a foldable substrate according to the present invention.

Before the invention is described in detail, it is to be understood that the invention is not limited to the particular component parts of the devices described or process steps of the methods described, as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a port" can include two or more such ports, and the like. In this specification and in the claims which follow, reference will be made to a number of terms which shall now be defined.

The use of novel construction and assembly techniques in the practice of the invention allows for a high degree of precision in the alignment of surface features other structures, which alignment has either been difficult or not possible in prior substrate-based devices. Thus, the term "microalignment" as used herein refers to precise alignment of structures, microstructures, and other surface features, including: the enhanced alignment of apertures, complementary channels, or compartments with each other; of inlet and/or outlet ports with annular seals, channels, or separation compartments; of external devices with ports, channels or separation compartments, and the like. The precision in alignment offered by the practice of the invention is believed to be in the range of less than 50 to 20 micrometers of error, and preferably less than 1 micrometer of error. In some instances, the microalignment has been so precise that alignment error is indistinguishable even under microscopic examination of transverse sections of bonded microstructures.

"Surface feature" refers to a structural feature on a component section that is distinguishable from the immediately surrounding portion of the component section. Examples of a surface feature include: corrugation, seal, aperture, recess, perforation, orifice, groove, chamber, compartment, depression, channel, pad, block, protrusion, nipple, and region (especially a region having a surface treatment). Note that the shape, dimensions, and symmetry of the various surface features illustrated and described herein will vary according to the implementation of the invention. A particular surface feature according to the present invention includes a specialized diaphragm and associated valve seat that are constructed for use in a novel microminiature valve.

"Microstructures" refers to surface features in the component sections having dimensions on the order of approximately 5 to 3000 micrometers and may include microchannels, microapertures, depressions, and the like. Microstructures in the form of microchannels of a semicircular cross section are etched by controlling the etch process. When a first channel is microaligned with a second channel thus formed, a fluid-handling conduit of highly symmetrical circular cross-section is defined which may be desirable for enhanced fluid flow in, for example, a sample processing or sample analysis system. Note that the shape, dimensions, and symmetry of the various microstructures contemplated herein will vary according to the implementation of the invention.

"Linear fold means" refers to means for dividing a substrate into at least two component sections whereby the operation of the linear fold means allows microalignment of complementary surface features in the component sections. Linear fold means can be formed in the substrate either by etching or by other methods of fabricating shaped apertures or depressions. Representative linear fold means that can be employed herein include a plurality of co-axially arranged apertures in component parts and/or a plurality of corresponding features in the substrate, e.g., depressions, grooves, slots, tunnels, hollow ridges, or the like. Accurate microalignment of two or more component sections is effected by forming at least one linear fold means provided between adjacent pairs of component sections, such that each pair of the component sections have surfaces that can be folded to overlie each other thereby forming composite micro-scale features such as apertures, compartments, or channels. Such linear fold means is preferably embodied by a row of spaced-apart perforations etched in a particular substrate, or by spaced-apart slot-like depressions or apertures etched so as to extend only part way through the substrate. The perforations or depressions can have circular, diamond, hexagonal or other shapes that promote hinge formation along a predetermined straight line. The linear fold means preferably includes, but is not limited to include, a "fold relief" which refers to a relief or similar excision of the substrate that facilitates folding of the substrate and the subsequent microalignment of the microstructures while maintaining the inextensibility of the substrate. The fold relief is effective at relieving the stress or deformation induced in the substrate in the immediate area of the fold axis by the folding motion.

"Foldable substrate" refers to a substrate which includes linear fold means, at least first and second component sections so defined by the linear fold means, and a characteristic of being foldable about the fold axis such that the substrate material is substantially inextensible in the plane of the fold axis. As a result, the microalignment of surface features upon closure of the component sections is maintained due to the lack of extension of the foldable substrate.

"Substantially inextensible" refers to a characteristic physical nature of a foldable substrate material that resists extension from the fold axis when the foldable substrate is subject to the typical forces which it is expected to receive during the assembly and use of an integrated assembly. Accordingly, miniaturized column devices are formed herein using suitable substrates which exhibit inextensibility when folded, such as metals and metal alloy substrates.

"Etched" and "etching" refer to surface material removal processes and include machining or cutting processes that provide surface features in a suitable substrate that are comparable to etched features. Etching is a preferred method for forming surface features in a wide variety of geometries. Any geometry which does not include undercutting may be provided using etching techniques. However, other forming methods for providing surface features are also contemplated, such as coining, fine blanking, milling, and abrading (using an abrasive in, e.g., an air or water stream.)

Etching includes such processes as common photolithography. Under the present invention, surface features are formed by imaging a lithographic mask onto a suitable substrate and then etching the substrate in areas that are unprotected by the lithographic mask. Such masks may define all of the etched features for a selected area of the substrate, for example, and the pattern may encompass multiple pairs of component sections to be created on the substrate, each of which feature complementary sets of microstructures. Alternatively, individual patterns such as an aperture pattern, a channel pattern, etc., may be placed side by side on a common mask for stepwise exposure of large substrates which are eventually processed to produce a plurality of individual substrates. An etching system employed in the invention generally includes beam delivery optics, alignment optics, a high precision and high speed mask shuttle system, and a processing chamber including mechanism for handling and positioning the substrate material.

"Electroforming" refers to a known fabrication technique wherein surface features or components are shaped by electrodeposition of a metal on a mandrel or pattern.

"Diffusion bonding" refers to a known bonding technique which involves the solid-state movement of the atoms and grain growth across a joint interface. Diffusion bonding provides bonded areas which are practically indistinguishable from the adjacent parent metal even on close metallurgical examination. In this regard, reference may be made to the patent to Owczarski et al., U.S. Pat. No. 3,530,568. A particularly preferred technique of diffusion bonding is described herein, wherein the surfaces to be joined are initially electroplated with a very thin surface layer (e.g., approximately 0.0003 inches or less) of nickel, nickel-phosphorous, or a nickel-cobalt alloy. The surface layer is formulated to melt at the desired diffusion bonding temperature, thus forming a transient liquid phase that fills surface defects (irregularities, asperities, and the like) at the interface of the microstructures in the surfaces to be joined. The molten surface layer subsequently re-solidifies, thus eliminating the surface defects.

A "multilayer" integrated assembly refers to an assembly formed from a foldable substrate whereby the component sections are subject to closure so as to form at least two bonded layers. A particularly preferred multilayer integrated assembly includes n component sections and n−1) linear fold means, wherein n equals three or more, wherein the component sections are closed upon one another in what is referred as a "Z-fold configuration."

"Intermediary substrate" refers to at least one added substrate layer interposed between two component sections, e.g., between first and second component sections, prior to closure and bonding of the two component sections so as to provide a composite structure. A "laminate" refers to the resulting multilayer structure, that is, a composite structure formed using a bondable intermediary substrate interposed between the first and second component sections. A laminate may include third and fourth component sections having a second intermediary substrate therebetween, and so forth. As will be described below with reference to FIG. 4, 1 particularly preferred intermediary substrate comprises an ultra-thin plate having a diaphragm integrated therein, thereby providing a laminate having intermediary layer of differing thickness than the surrounding layers. Further details of the construction of an integrated assembly, intermediary substrate, and linear fold means according to the present invention may be found in co-pending, commonly assigned U.S. patent application Ser. No. 08/846,607, filed on Apr. 30, 1997 and entitled "Multilayer Integrated Assembly Having Specialized Intermediary Substrate", the disclosure of which is incorporated herein by reference.

The present invention will find particular application in a variety of analytical systems that benefit from an integrated assembly that supports one or more fluid handling functions with respect to one or more fluid streams. Accordingly, the terms "fluid-handling" and "fluid-handling functions" refer to initiation, distribution, redirection, termination, control, detection, analysis, sensing, treatment, or similar functions with respect to one or more fluid streams.

"Analysis" refers to detecting and analyzing small and/or macromolecular solutes in a gas or liquid phase and may employ chromatographic separation means, electrophoretic separation means, electrochromatographic separation means, or combinations thereof. The terms "gas phase analysis" and "liquid phase analysis" are respectively used to refer to analyses which are done on either small and/or macromolecular solutes in the gas or liquid phase. Accordingly, "analysis" as used herein includes chromatographic separations, electrophoretic separations, and electrochromatographic separations.

Integrated assemblies constructed according to the invention are useful in an analysis system for detecting and analyzing small and/or macromolecular solutes in the gas or liquid phase and may employ chromatographic separation means, electrophoretic separation means, electrochromatographic separation means, or combinations thereof. In this regard, "chromatographic" processes generally comprise preferential separations of components, and include reverse-phase, hydrophobic interaction, ion exchange, molecular sieve chromatography and like methods.

"Fluid" refers to both gases and liquids, and thus to all types of fluids. The description of the invention will include a description of the arrangement, construction, or operation of certain fluid-handling devices, and in particular is directed to the control of a fluid stream by a microminiature valve, especially suited for use in a sample analysis system.

"Sample analysis systems" include systems for traditional gas and liquid chromatographic analysis, supercritical fluid chromatography, high-pressure gas chromatography (HPGC), high-performance liquid chromatography (HPLC), clinical analysis, electrophoresis, flow-injection analysis, laboratory water purification, manual and automated solid phase extraction (SPE) instruments, supercritical fluid extraction (SFE) instruments, spectrophotometers, protein or nucleic acid sequencers, and the like.

"Electrophoretic" separations refers to the migration of particles or macromolecules having a net electric charge where said migration is influenced by an electric field. Accordingly electrophoretic separations contemplated for use in the invention include separations performed in columns packed with gels (such as polyacrylamide, agarose and combinations thereof) as well as separations performed in solution.

"Electrochromatographic" separation refers to combinations of electrophoretic and chromatographic techniques.

"Motive force" refer to any means for inducing movement of a fluid along a path in a sample analysis system, and includes application of an electric potential across any portion of the path, application of a pressure differential across any portion of the path, or any combination thereof.

"Surface treatment" refers to preparation or modification of the surface of a component section, and in particular of a channel which will be in contact with a sample during separation, whereby the characteristics of the surface are altered or otherwise enhanced. Accordingly, "surface treatment" as used herein includes: physical surface coatings such as silication or silane coatings; physical surface adsorptions; covalent bonding of selected moieties to functional groups on the surface of channel substrates; methods of coating surfaces, including dynamic deactivation of channel surfaces, substrate grafting to the surface of channel substrates, and thin-film deposition of materials such as diamond or sapphire to channel substrates.

"Optional" or "optionally" means that the subsequently described feature or structure may or may not be present in the embodiment or that the subsequently described event or circumstance may or may not occur, and that the description includes both instances where said feature or structure is present and instances where the feature or structure is absent, or instances where the event or circumstance occurs and instances where it does not.

Referring generally to FIGS. 1–6, as will be appreciated by those working in the field of microminiature fluid handling devices, the methods described herein may be used to construct a novel microminiature valve, and in particular for construction of an integrated assembly for effecting fluid-handling functions wherein the assembly includes one or more novel microminiature valves embedded therein.

In the most basic practice of the integrated assembly, a housing for the microminiature valve may be provided in the form of a first component section superimposed upon a second component section and, and by closure of the component sections preferably (but not exclusively) with use of a linear fold means, certain complementary microstructures thereby superimposed will form a novel microminiature valve. According to the invention, the component sections may be sealed together to form a gas- or liquid-tight fluid handling functional device by using known pressure sealing or bonding techniques, by using external means to urge the pieces together (such as clips, tension springs or associated clamping apparatus), or by using adhesives well known in the art of bonding substrates and the like. In a particularly preferred embodiment, the component sections are hermetically sealed and bonded together via diffusion bonding and therefore avoid the problems associated with external means or by adhesives.

It will be readily appreciated that, although an array, channel, or compartment may be represented schematically in any illustration, a variety of surface features may be formed according to the invention, and accordingly such illustration is not intended to be limiting. Surface features may be etched or electroformed in a variety of configurations. Particular embodiments of the invention may comprise surface features in the form of an aperture provided so as to communicate with a microminiature valve, channel, or compartment to form an inlet port enabling the entry of fluid from an external source; a second aperture may be provided for communication with the valve, channel, or compartment to form an outlet port enabling passage of fluid to an external device. Ports or apertures may be provided for fluid communication between an exterior surface and an interior portion of the integrated assembly, or may simply communicate between compartments, channels, or conduits that are fully embedded within the integrated assembly; channels may be provided in configurations such as in a straight, serpentine, spiral, or any tortuous path; a channel may be formed in a wide variety of channel geometries including semi-circular, rectangular, rhomboid, and the like, and the channels may be formed in a wide range of aspect ratios. It is also noted that a component section may include a single surface feature to a variety of similar or dissimilar surface features, and will nonetheless fall within the spirit of the present invention.

Figure 2B:
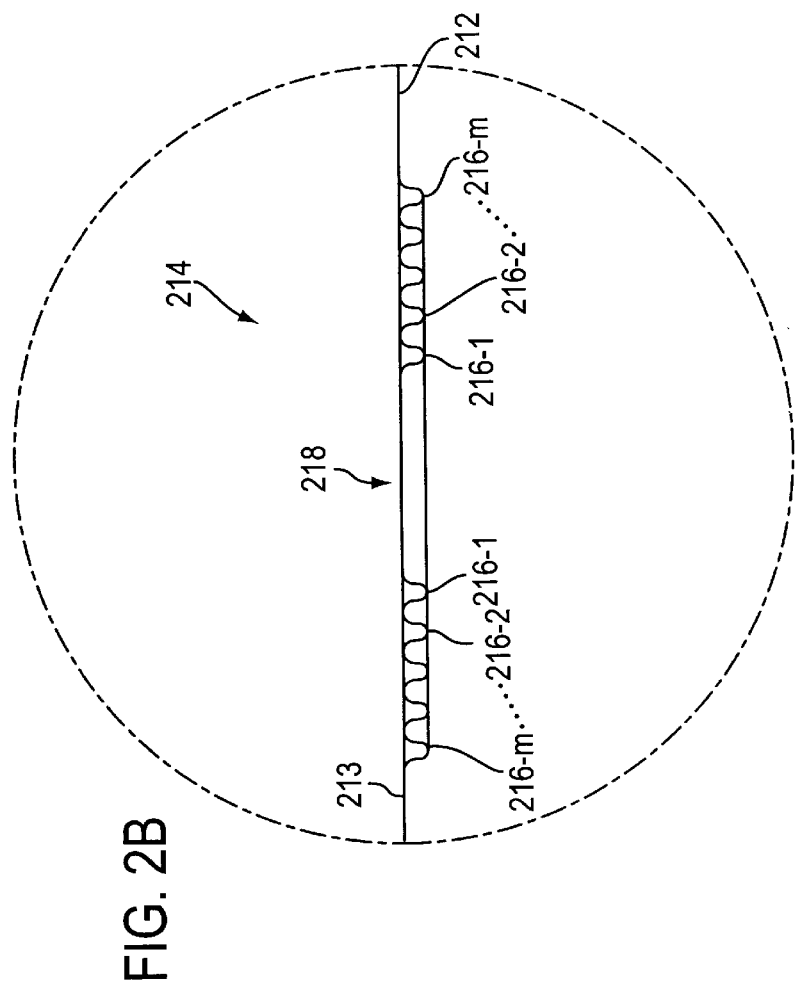
FIGS. 2A and 2B are side sectional and detailed side sectional views, respectively, of a diaphragm constructed for insertion in the integrated assembly of FIG. 1 prior to closure.
Figure 2A:
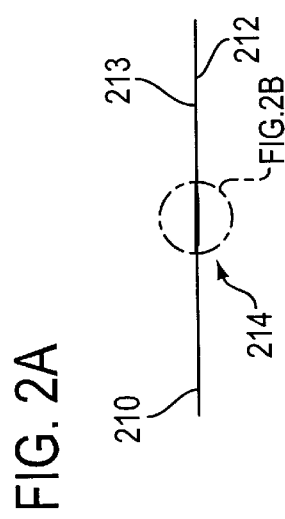

With reference now to FIGS. 1–2, a first preferred embodiment of a microminiature valve may be provided in a housing preferably constructed as an integrated assembly 102 that includes a linear fold means 104 located between first and second component sections indicated at 106 and 108 respectively. The integrated assembly 102 may thus be formed from a substantially planar foldable substrate such as a metallic plate which is etchable so as to enable the first and second component portions 106 and 108 to respectively include upper and lower interior surfaces, indicated at 110 and 112 respectively, in which microstructures and other miniaturized surface features may be etched. For example, a first channel pattern 114 is optionally etched in the first planar interior surface 110 and a second, complementary channel pattern 116 is optionally etched in the second planar interior surface 112. Closure and bonding of the first and second component portions 106,108 then create one or more conduits 118 capable of bearing a pressurized fluid.

In a particular feature of the invention, prior to closure, said upper and lower interior surfaces 110,112 are etched to include upper and lower cavity portions 120, 122 so as to accommodate a diaphragm 126. The first and second component halves 106, 108 are respectively etched to include certain additional surface features in locations selected according to the location of the diaphragm 126 and a fold axis defined by the linear fold means 104. The upper cavity portion 120 includes an upper cavity surface 110, and a control port 130; the lower cavity portion 122 includes a lower cavity surface 112 having a valve seat 124, wherein the valve seat 124 includes a central port 142 and a peripheral port 144. The diaphragm 126 is positioned between the first and second component halves 106,108 and is bonded to the first and second component sections 106,108 where the peripheral portion of the diaphragm 126 contacts the interior surfaces 110,112 as the first and second component sections 106,108, are closed, thereby providing a flexible but fluid-tight barrier between the upper and lower cavity portions 120,122.

With reference now to FIGS. 2–3, a preferred embodiment of a diaphragm 210 is prefabricated for disposition in microminiature valve. Preferably, the integrated assembly 102 includes a thin flexible plate having a first major surface 212 and a second major surface 213. Formed in the first major surface 212 is a concentric array 214 of m plural, raised annular seals 216-1, 216-2, 216-3, . . . 216-m . As may be understood with reference to FIG. 3, the diaphragm 210 may be electroformed so as to have a minimal thickness, in the range of 2 to 200 micrometers, and preferably on the order of about 25 micrometers, with an annular seal height in the range of 0.1 to 1 millimeters, and preferably about 0.1 millimeters, and it is thereby suited for mounting between the first and second component sections 106,108 of integrated assembly 102. The first and second component halves 106 and 108 are then folded together to form a laminate structure, thus fixing the diaphragm 210 as an intermediary layer, and are diffusion bonded to provide and integrated assembly such as the assembly 102 illustrated in FIG. 1. The periphery of the diaphragm 210 is accordingly supported between the first and second component sections 106,108 so as to span the upper and lower cavity portions 120,122. Accordingly, the diaphragm 210 is subject to concave or convex displacement in response to a differential pressure that may be induced between the upper and lower cavity portions 120,122.

The diaphragm 210 and the first and second component sections 106,108 are constructed so as to nominally position the annular seals 216-1, 216-2, 216-3 . . . closely proximate to the interior surface 112. The diaphragm 210 is located such that the concentric array 214 is coaxial with a control port 130 and a central port 142 . Means (not shown) may be attached to the control port 130 at the upper exterior surface 136 for providing a variable pressure in the upper cavity portion 120 so as to selectively displace the diaphragm 210 between closed and open positions, that is, between a first position wherein at least one of the annular seals 216-1, 216-2, 216-3 . . . contacts the interior surface 112, and a second position wherein the array 214 of annular seals 216-1, 216-2, 216-3 . . . is sufficiently spaced from interior surface 112 so as to allow fluid flow between central port 142 and a peripheral port 144. The central port 142 and the peripheral port 144 are located in the valve seat 124 in the lower interior surface 112 of the second component section 108 such that fluid communication between the exterior of the integrated assembly 102 and the lower cavity portion 122 allows a fluid stream to be provided to the lower cavity portion 122. The continuity and/4 the magnitude of the flow of such fluid stream is then subject to control by movement of the diaphragm 210.

For example, in a normally open microminiature valve, the annular seals 216-1, 216-2, 216-3, . . . 216-m in the array 214 would be situated away from the valve seat 124, whereupon an increase in the pressure differential between the upper cavity portion 120 and the lower cavity portion 122 distorts the diaphragm 210 towards the second interior surface 112 and causes at least one of the annular seals 216-1, 216-2, 216-3, . . . 216-m in the array 214 to contact the interior surface 112 so as to achieve a fluid-tight seal, thus blocking fluid flow between the central port 142 and the peripheral port 144. Alternatively, in a normally closed microminiature valve, at least one of the annular seals 216-1, 216-2, 216-3, . . . 216-m in the array 214 would be situated in contact with the valve seat 124 in the second interior surface 122 to effect a fluid-tight seal, whereupon a decrease in the pressure differential between the upper cavity portion 120 and the lower cavity portion 122 then distorts the diaphragm 10 up and away from the valve seat 124 in the second interior surface 112 and causes all of the annular seals 216-1, 216-2, 216-3, . . . 216-m in the array 14 to lose contact with the valve seat 124 so as to reverse a fluid-tight seal, thus allowing fluid flow between the central port 142 and the peripheral port 144.

Figure 4:
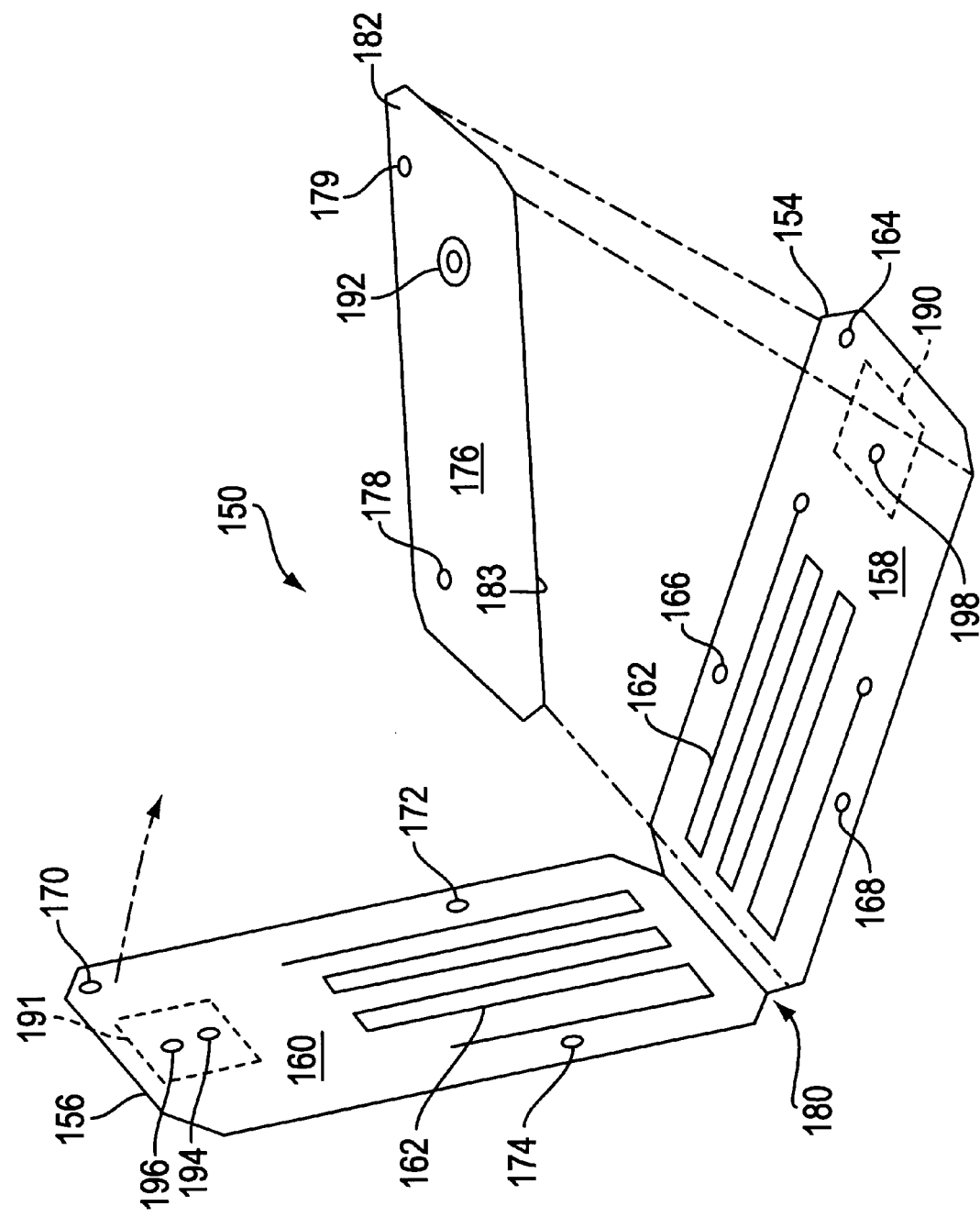
FIG. 4 is an exploded view of a second preferred embodiment of the integrated assembly that incorporates a diaphragm similar to the diaphragm of FIGS. 2–3 and formed on a intermediary substrate.

Referring now to FIG. 4, a second preferred embodiment of an integrated assembly 150 includes a foldable substrate 152 that receives an intermediary substrate 176 prior to closure and bonding. The integrated assembly 150 comprises first and second component sections, indicated at 154 and 156 respectively, each having a substantially planar interior surface indicated at 158 and 160 respectively. The interior surfaces may each comprise one or more optional complementary microstructures, such as channels 162. In particular, however, the foldable substrate 152 includes, as surface features therein, a lower cavity portion 190 and a corresponding upper cavity portion 191, a central port 194, a peripheral port 196, and a control port 198. The foldable substrate 152 includes linear fold means 180 to allow closure of the first and second support body halves 154 and 156 so as to superimpose complementary surface features defined by the microstructures etched on the first and second planar interior surfaces 158 and 160. The linear fold means 180 preferably includes a row of spaced-apart perforations provided in the foldable substrate 152. Alternatively, the linear fold means may include spaced-apart, slot-like depressions, grooves, or the like etched so as to extend only part way through the foldable substrate. The perforations or depressions may have circular, diamond, hexagonal or other shapes that promote hinge formation along a predetermined, straight line that constitutes the fold axis. A plurality of other surface features 164,170 may be provided in said first and second component sections 154 and 156 where said features are so arranged such that co-axial alignment thereof enables or corroborates the precise alignment of the component sections.

An intermediary substrate 176 is prefabricated and interposed between the component sections 154 and 156 such that a variety of surface features, generally indicated as 178 or 179, may interface with a corresponding surface feature or microstructure located on one of the first and second planar interior surfaces 158, 160. The intermediary substrate 176 is of course contemplated as being useful for providing one or more other specialized structural features that may or may not be feasible on the component sections 154 and 156, such as: a microstructure, conductor, semiconductor, insulator, electrode, sensor, sensor array, catalyst, orifice, screen, well, restriction, frit, perforation, porous section, or permeable or semi-permeable region. Alternatively, the prefabricated surface feature may define a particular surface region that includes a surface treatment such that a particular portion of the surface of the intermediary substrate 176 may function differently than other portions thereon. Such a surface feature optionally includes, for example, a surface treatment that is chemically or biologically-active, or includes a surface treatment that exhibits one or more particularly useful physical properties that may be difficult to provide in the foldable substrate 52, such as an optical, electrical, opto-electrical, magneto-optical, or magnetic characteristic.

In still another example, the intermediary substrate 176 can exhibit a dimensional characteristic (such as a lesser thickness) or material composition (such as a ceramic material) that differs from the corresponding characteristic in the foldable substrate, or is difficult or impractical to provide in the foldable substrate 152.

Hence, in a particular feature of the present invention, the intermediary substrate 176 is constructed as a thin, flexible diaphragm plate having a first major surface 182 and a second major surface 183. Formed in the first major surface 182 is a concentric array 192 of n plural, raised annular seals. The array 192 of annular seals is constructed and located so as to cooperate with control port 198, central port 194, and peripheral port 196 in the manner as described above with respect to the concentric array 214 in FIG. 1.

Figure 5:
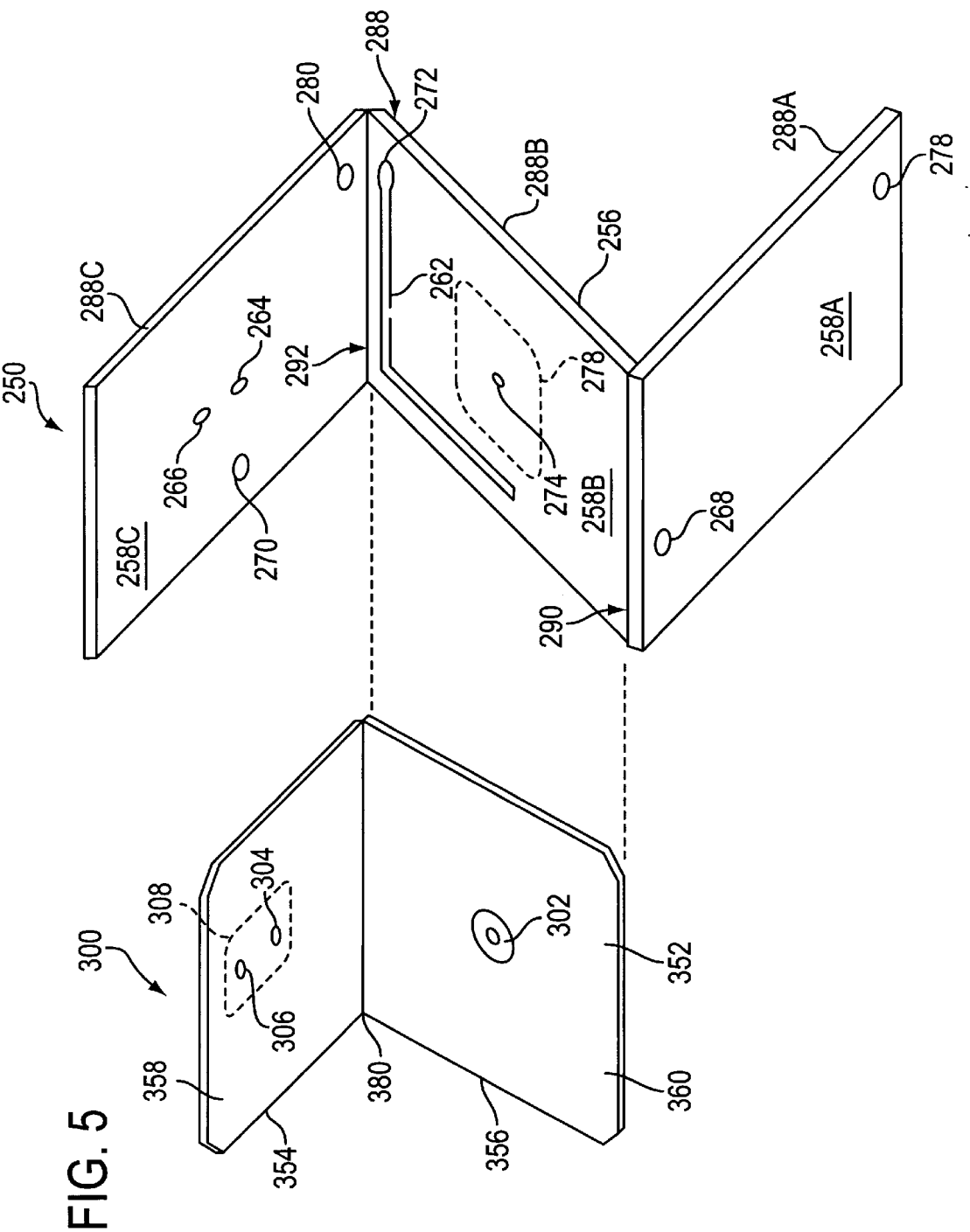
FIG. 5 is a perspective due of a third preferred embodiment of an integrated assembly that incorporates a novel microminiature valve in an intermediary substrate and a foldable substrate having a plurality of three or more component sections arranged in a Z-fold configuration.

Referring now to FIG. 5, a third embodiment of an integrated assembly 250 includes n component sections formed by definition of n–1) linear fold means in a single foldable substrate generally indicated at 288. In the illustrated embodiment, n is greater than two. The foldable substrate 288 thus comprises at least three component sections, e.g., a first portion 288A, second portion 288B, third portion 288C that may be closed upon one another according to a configuration considered herein as a "Z-fold" configuration. The second portion 288B includes first and second substantially planar opposing surfaces 256 and 258B, respectively, where the second portion is interposed between a first portion 288A and third portion 288C. The first and third portions 288A, 288C have respective planar surfaces 258A, 258C. The first portion 288A and the second portion 288B are separated by at least one linear fold means 290 such that the first portion can be readily folded to overlie the first substantially planar surface 256 of the second portion 288B. The third portion 288C and the second portion 288B are likewise separated by at least one linear fold means 292 such that the third portion can be readily folded to overlie the second substantially planar surface 258 of the second portion 288B. Surface features include: a channel 262, control port 274, and recess 278 in the planar surface 258B of the second portion 288B; ports 264 and 266 in the planar surface 258C of the third portion 288C; conduit means 272, comprising an etched aperture in the second portion 288B having an axis which is orthogonal to the first and second planar surfaces 256 and 258, communicates with a first end of the second channel 262; a first aperture 268 and a second aperture 270, etched in the third portion 288C, enables fluid communication with the channel 262.

A second planar device 300 is prefabricated according to the following description such that it may be closed, bonded, and inserted as an intermediary substrate into the open configuration of the second and third portions 288B and 288C in the first planar device 250, whereupon the first planar device 250 may then be folded, closed, and bonded to form an integrated assembly having at least one embedded microminiature valve. The second planar device 300 preferably comprises a foldable substrate 352 having first and second component sections, indicated at 354 and 356 respectively, each having a substantially planar interior surface indicated at 358 and 360 respectively. The foldable substrate 352 includes linear fold means 380 to allow the first and second component sections 354,356 to superimpose upon one another in a way that accurately aligns composite features defined by the microstructures etched on the first and second planar interior surfaces 358 and 360. The linear fold means 380 preferably includes a row of spaced-apart perforations located in the foldable substrate 352.

The interior surfaces 358,360 each comprise complementary microstructures that combine to form a major portion of a microminiature valve, preferably in the form of a concentric array 302 of annular seals, a central port 304, a peripheral port 306, and a valve seat 308. A control port 274, centrally located in a recess 278, is provided on the surface 258 of second portion 288B so as to be situated behind the second component section 356 and generally aligned with the location of the array 302 when the second planar device 300 is fitted into the integrated assembly 250. The control port 274 may be provided with a pressurized fluid by way of a conduit, similar to that exemplified by channel 262, that may be situated within the first portion 288A in the integrated assembly 250, for effecting variable displacement of the array 302 as described hereinabove. The central port 304 and the peripheral port 306 are aligned with respective first and second ports 264,266 so as to provide respective paths for communicating a signal fluid flow to the microminiature valve.

In the practice of the invention, external hardware may be provided to effect the fluid connections necessary for fluid communication with the microminiature valve and various other fluid handling functional devices such as channels, ports, and the like that are located within an integrated assembly. Typical connections may be to an external reservoir containing a fluid such as a carrier gas or a detector gas, an electrolyte solution, a flush solution, or a sample to be delivered into the integrated assembly. The microminiature valve described herein to be used as one of a variety of fluid handling functional devices internal to the integrated assembly, for effecting or assisting in, it e.g., modulation of carrier gas flow; modes for pressure injection, hydrodynamic injection, or electrokinetic injection; splitting, venting, or collecting fluid flow; and so on.

Also according to the invention, a variety of means for applying a motive force along the length of an internal channel or compartment may be associated with the microminiature valve in the integrated assembly. In this regard, a pressure differential may be applied along the entire length of a cavity or compartment by interfacing motive means with one or more of the aforementioned conduits and ports. It is also contemplated that external fluid coupling devices can effect fluid communication with or of the above described internal features by surface, edge, or butt-coupling such devices to respective apertures situated on the exterior of the integrated assembly.

What is claimed is:

1. A microminiature valve for controlling the flow of a signal fluid stream, comprising:

a housing including a cavity and a valve seat formed on a lower cavity surface, wherein the valve seat incorporates a central port and a peripheral port, a diaphragm peripherally mounted in the cavity so as to divide the cavity into an upper cavity section and a lower cavity section, the diaphragm having an array of a plurality of redundant, generally concentric, annular seals on an underside of the diaphragm, the diaphragm being positioned within the cavity so as to locate the array opposite the valve seat, wherein at least one of the annular seals is sufficiently positionable with respect to the valve seat for independently effecting a pressure tight barrier to fluid flow when impressed upon the valve seat, and wherein the upper cavity section includes a control port for supplying a pressurized control fluid to the upper cavity and accordingly to the upper side of the diaphragm so as to effect a pressure differential for movement of the diaphragm with respect to the valve seat;

Whereby the signal fluid stream, when provided between the central port and the peripheral port, is controlled by displacement of the array with respect to the valve seat, thereby controlling the flow of the signal fluid stream.

2. The valve of claim 1, wherein the diaphragm is provided in the form of a surface feature in an intermediary substrate constructed for use in an integrated assembly.

3. The valve of claim 1, wherein the diaphragm is composed of a metal.

4. A microminiature valve for controlling the flow of signal fluid comprising:

an enclosure including a cavity, the enclosure having a control port for carrying control fluid under pressure, the control port being in communication with the cavity, a diaphragm mounted in the enclosure with a major surface thereof facing the control port, the diaphragm extending across the cavity, the opposing major surface of the diaphragm having an array of redundant seals thereon; and a valve seat defining a portion of the enclosure cavity and having a central signal fluid carrying port and a peripheral signal fluid carrying port opening thereon in spaced relationship, such ports facing toward the control port and being on the opposite sides of the diaphragm from the control port, the redundant array of seals on the opposing major surface of the diaphragm facing the valve seat, the diaphragm being positioned with respect the valve seat so that when control fluid is released into the cavity urges the redundant array of seals into fluid tight sealing contact with the valve seat, the seals encompassing the central port when the redundant array of seals are in fluid tight sealing contact the valve seat to stop the flow of fluid to the peripheral signal fluid carrying port.

* * * * *